United States Patent
Srasra et al.

(10) Patent No.: US 7,960,585 B2
(45) Date of Patent: Jun. 14, 2011

(54) PROCESS FOR PREPARING SECONDARY AMIDES BY CARBONYLATION OF A CORRESPONDING TERTIARY AMINE

(75) Inventors: Mondher Srasra, Oud-Heverlee (BE); Pierre Jacobs, Gooik (BE); Bert Sels, Balen (BE); Maria Christina Jacoba Tielen, Linden (BE); Kristof Moonen, Hamme (BE); Peter Roose, Sint-Martens-Latem (BE); Ivan Vanden Eynde, Ghent (BE)

(73) Assignee: Taminco, Ghent (BE)

( * ) Notice: Subject to any disclaimer, the term of this patent is extended or adjusted under 35 U.S.C. 154(b) by 31 days.

(21) Appl. No.: 12/416,593

(22) Filed: Apr. 1, 2009

(65) Prior Publication Data

US 2010/0130785 A1    May 27, 2010

(30) Foreign Application Priority Data

Nov. 21, 2008    (EP) .................................... 08169717

(51) Int. Cl.
*C07C 231/10*    (2006.01)
(52) U.S. Cl. ...................................................... 564/132
(58) Field of Classification Search .................... 564/132
See application file for complete search history.

(56) References Cited

FOREIGN PATENT DOCUMENTS

| EP | 0 185 823 A1 | 7/1986 |
| EP | 0 365 382 A1 | 4/1990 |
| JP | 3-275656 A | 12/1991 |

OTHER PUBLICATIONS

Kobayashi et al., Journal of Organometallic Chemistry (1982), 231(1), p. C12-C14.*
Murahashi et al., Journal of the Chemical Society, Chemical Communications (1988), 24, p. 1578-1579.*

* cited by examiner

*Primary Examiner* — Brian J Davis
(74) *Attorney, Agent, or Firm* — Sughrue Mion, PLLC

(57) ABSTRACT

The present invention relates to a process for preparing secondary amides with good selectivity by carbonylating a corresponding tertiary amine with carbon monoxide in a reaction mixture in the presence of a metal catalyst and in the presence of a halogen containing promoter. The metal catalyst comprises palladium. A same or even a much better catalytic activity can be obtained with palladium than with the much more expensive rhodium, especially when the palladium is used in a low concentration. Moreover, also a good selectivity can be achieved.

21 Claims, No Drawings

PROCESS FOR PREPARING SECONDARY AMIDES BY CARBONYLATION OF A CORRESPONDING TERTIARY AMINE

The present invention relates to a process for preparing secondary amides by carbonylating a corresponding tertiary amine with carbon monoxide in a reaction mixture in the presence of a metal catalyst and in the presence of a halogen containing promoter.

Amides represent a large class of weakly basic nitrogen containing organic chemicals that find applications in large volumes, for instance as solvents and monomers, but also as more complex molecules in small volumes, for instance as pharmaceuticals, peptides, etc . . . Traditionally, N-alkyl amides are prepared using classic organic chemistry by reacting a suitable primary or secondary amine with a suitable carboxylic acid derivative such as a carboxylic acid or ester, an acid chloride or an acid anhydride. However, these methods are sometimes limited by the availability of suitable and readily available starting materials and suffer from low atom efficiency.

Also catalytic organometallic routes towards a wide variety of amides have been developed in more recent years. From these routes, aminocarbonylation is of special interest as carbon monoxide is used as a very cheap, readily available reagent to generate the amide functionality. This method involves a reaction of a primary or secondary amine with an aryl or alkyl halide and carbon monoxide. In a first step of the catalytic cycle, the metal is inserted in the carbon, halogen bond of the alkyl or aryl halide (oxidative addition). Subsequently, one molecule of carbon monoxide is transferred from the metal center to the alkyl or aryl radical (CO insertion). Finally, the newly formed carbonyl group is attacked by the amine and the final amide product is released from the metal centre together with one equivalent of HX, which readily reacts with another amine molecule in the reaction mixture to form an ammonium salt.

Because of the acid, base reaction between HX and amine, at least two equivalents of amine need to be added to the reaction mixture. Because of the low atom efficiency of the process and the high prices for halogenated raw materials, this method has only been used commercially for complex molecules (e.g. active ingredients in pharmaceuticals).

For production of dimethyl acetamide (DMAc) it is also known to prepare this secondary amide starting from the corresponding tertiary amine, namely from trimethyl amine (TMA). TMA is a cheap and readily available substrate. It is co-produced with methyl and dimethyl amines and has limited applications. For this reason, TMA has to be recycled to the reactor causing the size and the energy consumption of the plant to increase. The production of DMAc starting from TMA can thus offer an appropriate outlet for TMA and provide important energy and space/time savings to the parent amine production units.

The preparation of DMAc from TMA has been described in a number of patents. DE948056 reports the synthesis of DMAc from TMA and $CO/H_2$ with $(NMe_4)_2CoBr_2I_2$ as a catalyst. Only 90% yield of DMAc is reported in Example 6 at complete conversion of TMA after 7 h at 200° C. and 680 bars. Notwithstanding the high pressure, the catalyst used in this process has only a small catalytic activity. The turn over frequency (TOF—expressed as moles of converted product (TMA)/mole of catalytic metal/hour) achieved in the process of Example 6 was only in the order of 5 moles product/mole catalyst/hour. The long reaction time and very high pressure, however, restrict the industrial application of this process. Furthermore, undesired side products are produced. In Example 1 of DE948056, wherein the more reactive dimethyl or diethyl aniline was used instead of TMA, the activity of the catalyst was somewhat higher but as appears from Example 5, wherein the process was carried out at a lower pressure of 200 bars, a very high pressure was needed since otherwise the catalytic activity was much lower.

Several processes for converting TMA into DMAc have been reported based on the well-known carbonylation catalyst $Co_2(CO)_8$. However, this carbonyl complex is difficult to handle because of its instability to air and moderate heat. Upon decomposition and during the catalytic cycle of this metal, highly toxic, volatile metal species are formed. However, according to U.S. Pat. No. 3,407,231, $Co_2(CO)_8$ would allow the application of lower CO pressures: 95% conversion of TMA would be achieved at 225° C. and 138 bar. According to the description in the patent, the reaction runs without addition of a promoter. DMAc is recovered from the reaction mixture after removal of the volatile compounds in 99% purity. However, an impractical reaction time of 16 h is required. The TOF of the catalyst in this process is very low, namely only about 0.7 moles TMA/mole catalyst/hour. EP0185823 reports the use of water as a promoter together with $Co_2(CO)_8$ to achieve 92% conversion of TMA in only 5 h. The process was performed at a temperature of 250° C. and at a relatively high pressure of 172 bars. The catalyst activity was however still rather low, namely in the order of 5 moles TMA/mole catalyst/hour. Moreover, DMF (1%) is formed next to DMAc. It should be noted that relatively high catalyst loadings are reported for these cobalt based processes, which may be explained by the quite low activity of the cobalt catalysts.

Results with other metals as a catalyst are very scarce. JP 46 043 527 reports only moderate yields of DMAc from the reaction of TMA and CO over a $HgI_2$ catalyst at 260° C. Only one noble metal is used as a catalyst for the carbonylation of a tertiary amine. JP 3 275 656 A reports 56% yield of DMAC at 72% conversion of TMA using $RhCl_3$ as a catalyst and methyl iodide as a promoter at 270° C. DMF and N-methyl acetamide are formed as side products in 1 and 4% yield respectively. The catalytic activity of the rhodium catalyst is much higher than that of the above described cobalt catalysts. The TOF which could be achieved with the rhodium catalyst was indeed about 19 moles TMA/mole catalyst/hour. Notwithstanding this higher activity, the investment cost of a potential industrial installation is however still quite high since rhodium is known as a very expensive material. Its use as a catalyst therefore limits the economic attractiveness of the process. Recently, CN101003491A reported the use of a combination of Rh halogenides with smaller or equal amounts of Ir halogenides for the catalytic conversion of TMA into DMAc under very similar conditions.

An object of the present invention is to provide a method for carbonylating a tertiary amine wherein use is made of a catalyst which is a good or even a better alternative for rhodium, the catalyst being in particular less expensive than rhodium and enabling to achieve a similar or even a higher TON than with rhodium.

This object is achieved in accordance with the present invention by using a catalyst which comprises palladium. The invention therefore relates to a process for preparing a secondary amide with the following formula

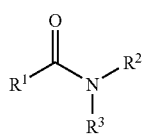

wherein
- $R^1$ is an aromatic group or a straight or branched aliphatic carbon chain which comprises at least one carbon atom and which may be substituted or not;
- $R^2$ and $R^3$ are, independent from one another, an aromatic group or a further straight or branched aliphatic carbon chain which comprises at least one carbon atom and which may be substituted or not, or $R^2$ and $R^3$ form a cycle containing the amide nitrogen, which process comprises the step of carbonylating a tertiary amine of the formula

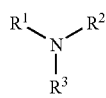

with carbon monoxide in a reaction mixture in the presence of a catalyst which comprises palladium and in the presence of a halogen containing promoter.

It was found that palladium, as a relatively cheap noble metal, was able to carbonylate trimethyl amine into dimethyl acetamide at reaction rates and selectivities that were as good or even superior to that for expensive noble metals such as Rh or Ir. A same or even a much better catalytic activity (TOF) could be achieved with palladium than with rhodium. Furthermore, using Pd as a catalyst, also higher tertiary amines and aromatic tertiary amines, could be carbonylated with good yield and selectivity to the corresponding secondary amides. In all the reactions mentioned above, a suitable halogen containing promoter is used, which is only required in subequivalent amounts. Therefore, the current invention describes a completely atom efficient synthesis of secondary amides from the corresponding tertiary amines.

In a preferred embodiment of the process according to the invention, the reaction mixture comprises less than 5000 ppm, preferably less than 3000 ppm, more preferably less than 1500 ppm and most preferably less than 750 ppm of palladium which is dispersed or dissolved in the reaction medium.

It was found quite surprisingly that the catalytic activity of the palladium catalyst increased considerably when lowering its concentration, more particularly even to such an extent that when lowering the amount of catalyst in the reaction mixture, similar or only somewhat smaller reaction rates could be achieved. This is a very important finding since a smaller amount of catalyst results in lower costs and requires moreover less efforts to recycle and recover the catalyst. Palladium proved to be active in the process according to the invention at concentrations of 10 ppm or even lower. This was not reported earlier for other noble metals such as Rh or Ir and favours the economics of a Pd based carbonylation process. The palladium is preferably added in a concentration of at least 1 ppm, more preferably in a concentration of at least 10 ppm.

The palladium can be added in the form of an inorganic salt, exemplified but not limited by $PdCl_2$, $PdBr_2$, $PdI_2$, $Pd(OAc)_2$, $PdSO_4$, $(NH_4)_2[PdCl_6]$, $(NH_4)_2[PdCl_4]$, $PdC_2O_4$, $Pd(acac)_2$; in the form of an oxide, in the form of a metal deposited on a support such as carbon, alumina, silica, zeolite, clay, porous polymer, hybrid polymer, etc . . . or in the form of a Pd(0) complex carrying organic ligands, exemplified but not limited by $Pd(PPh_3)_4$. Also preformed metal complexes, such as $PdCl_2(CH_3CN)_2$, dichloro ethylenediamine palladium, dichloro bispyridine palladium, $Pd(TMA)_2Cl_2 Pd(NH_3)_4Cl_2$, $Pd(NH_3)_2Cl_2$, etc . . . can be added as a catalyst precursor. Carbon monoxide and amines are known to behave as ligands to transition metal complexes.

The halogen containing promoter is preferably present in said reaction mixture in a molar ratio of greater than 0.1, preferably greater than 1 and more preferably greater than 5 with respect to the catalyst metal. This ratio is preferably smaller than 10000, and more preferably smaller than 2000.

The halogen containing promoter which is present in the reaction mixture comprises preferably a halide of formula $R^1X$ wherein X is I, Br or Cl, the halide of formula $R^1X$ being preferably $R^1I$. The hydrocarbon group, in particular the alkyl or aryl group on the halide thus preferably corresponds to the hydrocarbon group on the amine in which CO insertion is desired. Suitable halides are iodides, bromides or chlorides such as methyl iodide, ethyl iodide, propyl iodide, . . . , benzyl iodide, phenyl iodide, . . . The best results are obtained with alkyl iodides, although the corresponding chlorides and bromides can also be used.

The halogen containing promoter can be added as such to the reaction mixture. However, it is also possible to add compounds which produce the promoter in situ in the reaction mixture. Alkyl and benzyl halides are for example known to react easily with tertiary amines with the formation of tetraalkyl ammonium halide salts. Therefore, also these salts can be added to the reaction system instead of the parent alkyl halide. Without any limitation, suitable tetraalkyl ammonium halide salts can be found in the next series: tetramethyl ammonium iodide (TMAI), tetraethyl ammonium iodide, tetrapropylammonium iodide, tetrabutyl ammonium iodide, benzyl trimethyl ammonium iodide, . . . and the corresponding chloride and bromides. Also the corresponding tetraalkyl phosphonium halides may be used with the same purpose. Furthermore, other agents that may be able to generate alkyl or aryl halides in the reaction mixture under the reaction conditions applied can be used as a promoter. These agents are exemplified by but not limited to $I_2$, $Br_2$, $Cl_2$, LiI, NaI, KI, HI. Also acid halides of formula $R^1COX$, that are possible intermediates in the catalytic cycle, can be added to generate the promoter in the reaction mixture.

When sufficient amounts of tertiary amine are supplied to the reaction mixture, the promoter is regenerated in the reaction mixture under normal catalytic activity. This means that it can be added in so-called subequivalent amounts: less mole of promoter is present in the reactor than mole TMA is converted. However, when the reaction mixture is depleted from tertiary amine, side reactions start to occur which can be attributed to the consumption of the promoter.

This catalyst/promoter combination can be used for the carbonylation of tertiary amines of the general formula

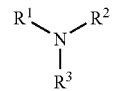

wherein $R^1$, $R^2$, $R^3$ are not H, but independently a saturated or unsaturated, branched or unbranched carbon chain containing from 1 to 23 carbon atoms or an aromatic ring. The carbon chains may also be substituted for example with a phenyl group, an alkoxy, a carboxy, an amido group, . . . , and may thus consist for example of a benzyl group, a 2-methoxyl ethyl group, a carboxy methyl group, . . . . $R^2$ and $R^3$ may also form a cyclic structure. Furthermore, $R^1$, $R^2$, $R^3$ can contain heteroatoms, such as oxygen in their chains, for instance ether linkages. Such chains fall also under the expression "carbon chains", the number of heteroatoms being not included in the number of carbon atoms.

The resulting amides then comprise at least the amide having the following formula:

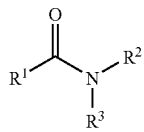

wherein $R^1$, $R^2$, $R^3$ are defined as in the parent amine.

If $R^1$, $R^2$, $R^3$ are not the same, or if the halogen containing promoter comprises $R^2$ or $R^3$ groups which are different from $R^1$, then the obtained amides may also comprise one or more of the amides of the following formulas:

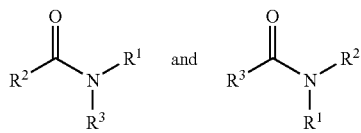

wherein $R^1$, $R^2$, $R^3$ are again defined as in the parent amine.

These amides are all secondary amides. By the expression "secondary amide" is meant in the present specification an amide which has no hydrogen on the amide N.

In one particular embodiment $R^1$, $R^2$ and $R^3$ are independently a straight or branched aliphatic carbon chain containing 1 to 23 carbon atoms, preferably 1 to 9 carbon atoms, the carbon chains being preferably unsubstituted. The $R^1$, $R^2$ and $R^3$ groups are preferably the same, and are more preferably all methyl groups.

In another particular embodiment, $R^1$ is a straight or branched aliphatic carbon chain containing 1 to 23 carbon atoms, preferably 1 to 9 carbon atoms, and $R^2$ and $R^3$ form an azacycle together with the amide nitrogen atom, the carbon chain being preferably unsubstituted. An example hereof is N-acetyl piperidine produced from N-methyl piperidine.

In still another particular embodiment, $R^1$ is a straight or branched aliphatic carbon chain containing 1 to 23 carbon atoms, preferably 1 to 9 carbon atoms, and $R^2$ and $R^3$ form a heterocycle together with the amine nitrogen atom, which heterocycle contains at least one additional heteroatom, in particular nitrogen or oxygen, and the carbon chain being preferably unsubstituted. An example of such a tertiary amine is N-methyl morpholine producing N-acetyl morpholine after the carbonylation step.

In another particular embodiment, $R^1$ and $R^2$ are each a straight or branched aliphatic carbon chain containing 1 to 23 carbon atoms, preferably 1 to 9 carbon atoms, and $R^3$ is an aromatic group, in particular a phenyl or a functionalized phenyl group, such as chlorophenyl, methoxyphenyl, fluorophenyl, . . . or a straight or branched carbon chain which contains 1 to 23 carbon atoms, preferably 1 to 9 carbon atoms, and which is substituted with an aromatic group, in particular with a phenyl group or with a functionalized phenyl group. An example of such a tertiary amine is N,N-dimethyl N-benzylamine producing N,N-dimethyl-2-phenyl acetamide and N-methyl-N-benzyl-2-phenyl acetamide after the carbonylation step. Another example is N,N-dimethyl aniline.

The reaction is performed in a closed vessel under a CO containing atmosphere at a pressure of higher than 20 bar, more preferably higher than 50 bar. The total pressure that can be applied is only limited by the equipment that is used. The atmosphere may contain only CO or may also be a $CO/H_2$ mixture. Such a $CO/H_2$ mixture results however in a slightly lower activity and selectivity. Higher amounts of formamides are produced as a side product.

The carbonylation reaction is carried out at a temperature higher than the temperature at which the catalyst becomes active. This temperature depends on the type of tertiary amine. For aromatic amines this minimum temperature is generally lower whilst for alkyl amines it is generally higher. Amines containing heteratoms such as oxygen show an intermediate behaviour. A possible explanation of this different activation temperature is that aromatic amines seem to be very efficient ligands and give rise to active complexes at lower temperatures, while alkyl amines often need higher temperatures in order to obtain a relevant catalytic system. The carbonylation step is carried out at a temperature higher than 120° C. and more preferably at a temperature higher than 180° C., especially when the tertiary amine is not aromatic.

Above the temperature required for catalyst activation, the activity of the catalytic system increases when the temperature is increased. The temperature is however preferably maintained below 285° C. since at higher temperatures, a slight decrease in selectivity was observed.

The reaction medium preferably contains a solvent. Advantageously, the product amide is used as the solvent. However, also other amides than the expected product amides can be used. Excellent results are obtained when NMP is used as a solvent.

When using the current catalytic system under the appropriate reaction conditions, the amount of side products formed is surprisingly low. The major side product amide is the corresponding primary amide (in particular the corresponding N-alkyl alkylamide) which has lost one alkyl or aryl group. Other side products include carboxylic acids, nitriles and formamides. The latter are known to be formed from secondary amines and carbon monoxide.

EXAMPLES

Example 1

A 50 mL autoclave is charged with 0.45 mmol of catalyst and 4.3 mmol of a suitable halogen containing promoter. After the vessel is closed, it is flushed four times with carbon monoxide (10 bar). Then 17.5 mL of a 7.3% (by mass) TMA in NMP solution is added through a septum by means of a syringe. The mixture thus contains 2736 ppm of the catalyst metal. It is stirred vigorously for 10 minutes at room temperature and charged with 65 bar of carbon monoxide. The reaction mixture is heated to 240° C. in 24 minutes. At the end of the reaction, the mixture is cooled to 0° C., degassed properly and analyzed via GC. This example shows the higher activity and selectivity of the $PdCl_2$/TMAI system in comparison with the other metal iodide source combinations. It especially shows that with a cheaper Pd-catalyst a same or even a higher catalyst activity can be obtained than with a more expensive Rh-catalyst.

| Catalyst | Promoter | Time (min) | Yield (%) | | | | | TOF (h$^{-1}$) |
|---|---|---|---|---|---|---|---|---|
| | | | DMAc | MMAc | DMF | AcN | HOAc | |
| PdCl$_2$ | TMAI | 130 | 96.0 | 0.0 | 0.0 | 0.0 | 5.2 | 24 |
| PdCl$_2$ | MeI | 50 | 83.9 | 3.5 | 0.0 | 0.0 | 14.7 | 87 |
| PdCl$_2$ | I$_2$ | 96 | 63.7 | 18.0 | 1.1 | 1.9 | 5.9 | 23 |
| [(C$_6$H$_5$)$_3$P]$_4$Pd | TMAI | 216 | 67.0 | 6.1 | 1.5 | 0.0 | 12.2 | 9 |
| RhCl$_3$ | TMAI | 114 | 94.3 | 0.4 | 0.5 | 0.0 | 10.9 | 22 |
| AuCl$_3$ | TMAI | 156 | 19.8 | 2.1 | 0.0 | 0.0 | 0.0 | 3 |
| H$_2$IrCl$_3$ | TMAI | 191 | 39.8 | 1.4 | 5.2 | 0.0 | 0.0 | 6 |

DMAc, N,N-dimethyl acetamide;
MMAc, N-methyl acetamide;
DMF, N,N-dimethyl formamide;
ACN, Acetonitrile;
HOAc, Acetic acid.

Example 2

These experiments were performed with PdCl$_2$ as a catalyst, TMAI as a promoter (TMAI:Pd=10) and NMP as the solvent. Firstly, a 50 mL autoclave is charged 0.45 mmol of PdCl$_2$ and 4.3 mmol of TMAI. After the vessel is closed, it is flushed four times with carbon monoxide (10 bar). Then 17.5 mL of the reactant in NMP solution is added through a septum by means of syringe. The mixture is stirred vigorously for 10 minutes at room temperature and charged with 65 bar of carbon monoxide. The reaction mixture is heated to 240° C., unless stated otherwise in the table, in 24 minutes. At the end of the reaction, the mixture is cooled to 10° C., degassed properly and analyzed via GC. This example shows that our catalyst system can be used for the carbonylation of several tertiary amines.

| Reactant (% in NMP) | Reaction time (min) | Conversion (%) | Yield of main products (mol %) |
|---|---|---|---|
| DMAn* (12.0) | 75 | 100 | 92% N-methyl-N-phenyl acetamide |
| DMEA (7.3) | 77 | 100 | 74% N-methyl-N-ethyl acetamide<br>21% N,N-diethyl acetamide |
| TEA (12.1) | 140 | 100 | 43% N,N-diethyl acetamide<br>37% N,N-diethyl propionamide<br>12% N-methyl-N-ethyl acetamide |
| N,N-dimethyl nonylamine (17.0) | 170 | 100 | 67% N-methyl-N-nonylacetamide |
| N-Methyl Piperidine (9.9) | 180 | 88 | 75% N-acetyl piperidine |
| N-methyl Morpholine (10.0) | 90 | 100 | 60% N-Acetyl Morpholine |
| N,N-dimethyl N-benzylamine (13.5) | 210 | 77 | 18% N,N-dimethyl-2-phenyl acetamide<br>8% N-methyl-N-benzyl-2-phenyl acetamide |

*reaction performed at 190° C.
DMAn, N,N-dimethyl aniline;
DMEA, dimethylethylamine; Triethylamine.

Example 3

A 50 mL autoclave is charged with 0.45 mmol of PdCl$_2$ as catalyst and 4.3 mmol of TMAI as promoter. After the vessel is closed, it is flushed four times with carbon monoxide (10 bar). Then 17.5 mL of a 7.3 or 8.3% (by mass) TMA in NMP or in DMAc solution is added through a septum by means of a syringe. The mixture is stirred vigorously for 10 minutes at room temperature and charged with 65 bar of carbon monoxide. The reaction mixture is heated to 240° C. and CO consumption was monitored via the pressure decrease. At approximately 50% conversion, the reaction mixture was cooled to 0° C., degassed properly and analyzed via GC. This example shows that in addition to NMP, DMAc can be used also as solvent for this reaction.

| Solvent | t (min) | Selectivity (%) | | | |
|---|---|---|---|---|---|
| | | DMAc | MMAc | DMF | HOAc |
| NMP | 85 | 94.5 | 0.3 | 0.0 | 5.2 |
| DMAc | 65 | 94.5 | 1.0 | 2.1 | 2.4 |

Example 4

This example demonstrates the possibility to increase the catalyst activity by lowering the catalyst concentration.

A 50 mL autoclave is charged with a suitable amount (see table) of PdCl$_2$ as a catalyst and 4.3 mmol of TMAI a suitable promoter. After the vessel is closed, it is flushed four times with carbon monoxide (10 bar). Then 17.5 mL of a 7.0% (by mass) TMA in NMP solution is added through a septum by means of a syringe. The mixture is stirred vigorously for 10 minutes at room temperature and charged with 65 bar of carbon monoxide. The reaction mixture is heated to 240° C. in 24 minutes. From that point, the time was monitored to consume 9 bars of CO pressure (t9). The mixture was allowed to react further to full conversion. At the end of the reaction, the mixture is cooled to 0° C., degassed properly and analyzed via GC. This example shows that the activity of the Pd catalyst increases considerably as its concentration decreases, even to such an extent that substantially the same amount of amide can be produced with a smaller amount of catalyst.

| [Pd] (ppm) | TOF (h$^{-1}$) | t9 (min) | % yield DMAc |
|---|---|---|---|
| 377 | 158 | 86 | 94 |
| 171 | 238 | 105 | 90 |
| 41 | 1100 | 118 | 97 |

Example 5

Recycling of the Catalyst

NMP (252.2 g), TMAI (11.4 g, 57 mmol) and PdCl$_2$ (1.18 g, 6.7 mmol) were added to a 1 L Parr reactor equipped with a magnetically coupled stirrer, sampling tube and feed vessel. After the reactor was closed, it was flushed three times with CO. Then, 20.1 g (0.34 mol) of TMA was added through the feed vessel and pressure was brought to approx. 60 bar with CO. The reaction mixture was heated to 240° C. and CO consumption was monitored via the pressure decrease. At approximately 80% conversion, the reaction mixture was cooled down. To start a second trial, additional TMA was added, pressure was readjusted and the mixture was heated again. After the third trial, analysis showed that sufficient TMA was still present to perform a fourth trial.

The results in the table below clearly show that PdCl$_2$ and TMAI act as a true catalytic system that can be recycled while keeping its excellent selectivity. Both species can be used in subequivalent amounts.

| Trial | TMA added | TMA | DMAc | MMAc | DMF | HOAc |
|---|---|---|---|---|---|---|
| 1 | 20.1 g | 1.65% | 6.66% | 0.04% | 0.02% | 0.11% |
| 2 | 20.2 g | 3.80% | 11.36% | 0.05% | 0.21% | 0.09% |
| 3 | 19.4 g | 8.15% | 14.06% | 0.09% | 0.46% | 0.08% |
| 4 | 0 g | 0.24% | 19.69% | 0.16% | 0.54% | 0.09% |

The invention claimed is:

1. A process for preparing a secondary amide with the following formula

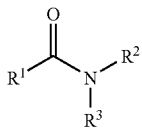

wherein
R$^1$ is an aromatic group or a straight or branched aliphatic carbon chain which comprises at least one carbon atom and which may be substituted or not;
R$^2$ and R$^3$ are, independent from one another, an aromatic group or a further straight or branched aliphatic carbon chain which comprises at least one carbon atom and which may be substituted or not, or R$^2$ and R$^3$ form a cycle containing the amide nitrogen,
which process comprises the step of carbonylating a tertiary amine of formula

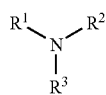

with carbon monoxide in a reaction mixture in the presence of a catalyst which comprises palladium and in the presence of a halogen containing promoter, the reaction mixture comprising less than 750 ppm of palladium.

2. A process according to claim 1, wherein said halogen containing promoter comprises a halide of formula R$^1$X wherein X is I, Br or Cl.

3. A process according to claim 1, wherein the halogen containing promoter is introduced in the reaction mixture by adding one or more compounds from the group consisting of halides of formula R$^1$X, halides of formula R$_4^1$N$^+$X$^-$, phosphonium halide salts of formula R$_4^1$P$^+$X$^-$, X$_2$, metal halide salts, and acid halides of formula R$^1$COX to the reaction mixture, the halogen being chlorine, bromine or iodine.

4. A process according to claim 3, wherein the halogen containing promoter is introduced in the reaction mixture by adding the halide of formula R$^1$X to the reaction mixture.

5. A process according to claim 1, wherein R$^1$, R$^2$ and R$^3$ are independently a straight or branched aliphatic carbon chain containing 1 to 23 carbon atoms.

6. A process according to claim 5, wherein the carbon chains are not substituted.

7. A process according to claim 5, wherein at least the carbon chain of the R$^1$ group is substituted with an aromatic group.

8. A process according to claim 1, wherein R$^1$ is a straight or branched aliphatic carbon chain containing 1 to 23 carbon atoms and R$^2$ and R$^3$ form an azacycle together with the amide nitrogen atom.

9. A process according to claim 1, wherein R$^1$ is a straight or branched aliphatic carbon chain containing 1 to 23 carbon atoms and R$^2$ and R$^3$ form a heterocycle together with the amine nitrogen atom, which heterocycle contains at least one additional heteroatom.

10. A process according to claim 1, wherein said catalyst comprises Pd(II).

11. A process according to claim 1, wherein said catalyst comprises Pd(0).

12. A process according to claim 1, wherein the halogen containing promoter is present in said reaction mixture in a molar ratio of greater than 0.1 with respect to the catalyst metal.

13. A process according to claim 1, wherein the carbonylation step is carried out at a temperature lower than 285° C.

14. A process according to claim 1, wherein the carbonylation step is carried out at a pressure higher than 20 bars.

15. A process according to claim 1, wherein R$^1$, R$^2$ and R$^3$ are methyl groups.

16. A process according to claim 10, wherein said palladium is added to said reaction mixture as an inorganic salt selected from the group consisting of PdCl$_2$, PdBr$_2$, PdI$_2$, Pd(OAc)$_2$, PdSO$_4$, (NH$_4$)$_2$[PdCl$_6$], (NH$_4$)$_2$[PdCl$_4$], Pd(acac)$_2$ and PdC$_2$O$_4$.

17. A process according to claim 11, wherein said palladium is added to said reaction mixture as a complex and/or as a metal deposited on a support.

18. A process according to claim 1, wherein the carbonylation step is carried out at a temperature higher than 120° C.

19. A process according to claim 18, wherein the carbonylation step is carried out at a temperature higher than 180° C.

20. A process according to claim 14, wherein the carbonylation step is carried out at a pressure higher than 50 bars.

21. A process according to claim 1, wherein R$^1$ is a saturated straight or branched aliphatic carbon chain containing from 1 to 23 carbon atoms.

* * * * *